(12) United States Patent
Siegal et al.

(10) Patent No.: US 9,254,138 B2
(45) Date of Patent: Feb. 9, 2016

(54) TISSUE DISRUPTION DEVICE AND CORRESPONDING METHODS

(71) Applicant: NLT SPINE LTD., Kfar Saba (IL)

(72) Inventors: Tzony Siegal, Moshav Shoeva (IL); Oded Loebl, Tel Mond (IL); Didier Toubia, Raanana (IL)

(73) Assignee: NLT Spine Ltd., Kfar Saba (IL)

( * ) Notice: Subject to any disclaimer, the term of this patent is extended or adjusted under 35 U.S.C. 154(b) by 0 days.

(21) Appl. No.: 14/459,336

(22) Filed: Aug. 14, 2014

(65) Prior Publication Data

US 2015/0012000 A1    Jan. 8, 2015

Related U.S. Application Data

(63) Continuation of application No. 13/512,894, filed as application No. PCT/IB2012/052406 on May 14, 2012, now Pat. No. 8,845,638.

(60) Provisional application No. 61/485,140, filed on May 12, 2011.

(51) Int. Cl.
| | |
|---|---|
| *A61B 17/16* | (2006.01) |
| *A61B 17/32* | (2006.01) |
| *A61B 17/00* | (2006.01) |
| *A61B 17/29* | (2006.01) |
| *A61B 19/00* | (2006.01) |

(52) U.S. Cl.
CPC ......... *A61B 17/1671* (2013.01); *A61B 17/1631* (2013.01); *A61B 17/32002* (2013.01); *A61B 2017/00398* (2013.01); *A61B 2017/2927* (2013.01); *A61B 2017/2936* (2013.01); *A61B 2017/2943* (2013.01); *A61B 2017/320032* (2013.01); *A61B 2019/304* (2013.01)

(58) Field of Classification Search
CPC ........... A61B 17/1631; A61B 17/1671; A61B 17/32002
See application file for complete search history.

(56) References Cited

U.S. PATENT DOCUMENTS

| | | | |
|---|---|---|---|
| 6,923,813 B2 * | 8/2005 | Phillips et al. | 606/86 R |
| 7,922,720 B2 * | 4/2011 | May et al. | 606/80 |
| 8,123,750 B2 * | 2/2012 | Norton et al. | 606/80 |
| 2005/0261692 A1 | 11/2005 | Carrison et al. | |

FOREIGN PATENT DOCUMENTS

| | | |
|---|---|---|
| WO | 2008144709 | 11/2008 |
| WO | 2010135507 | 11/2010 |

* cited by examiner

*Primary Examiner* — Andrew Yang
(74) *Attorney, Agent, or Firm* — Mark M. Friedman

(57) ABSTRACT

A tissue disruption device (10) for deployment via a rigid conduit (100) includes a rotary tissue disruptor (12) insertable along the conduit with its axis of rotation (14) parallel to the direction of conduit elongation (16). An angular displacement mechanism allows selective displacement of the rotary tissue disruptor (12) such that the axis of rotation (14) sweeps through a range of angular motion. A rotary drive is linked to the rotary tissue disruptor so as to drive the rotary tissue disruptor in rotary motion while the rotary tissue disruptor is at a range of angular positions within the range of angular motion.

31 Claims, 19 Drawing Sheets

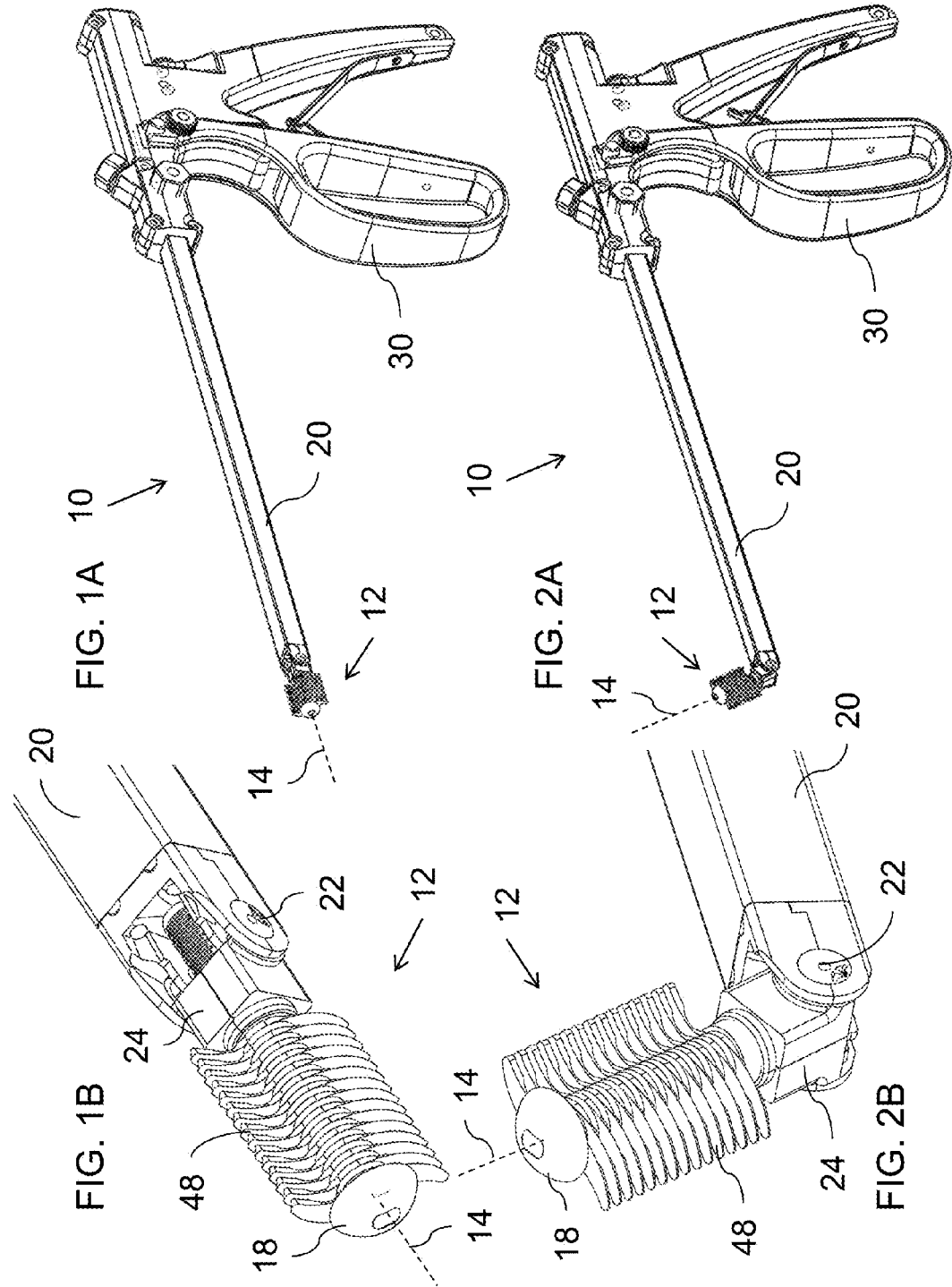

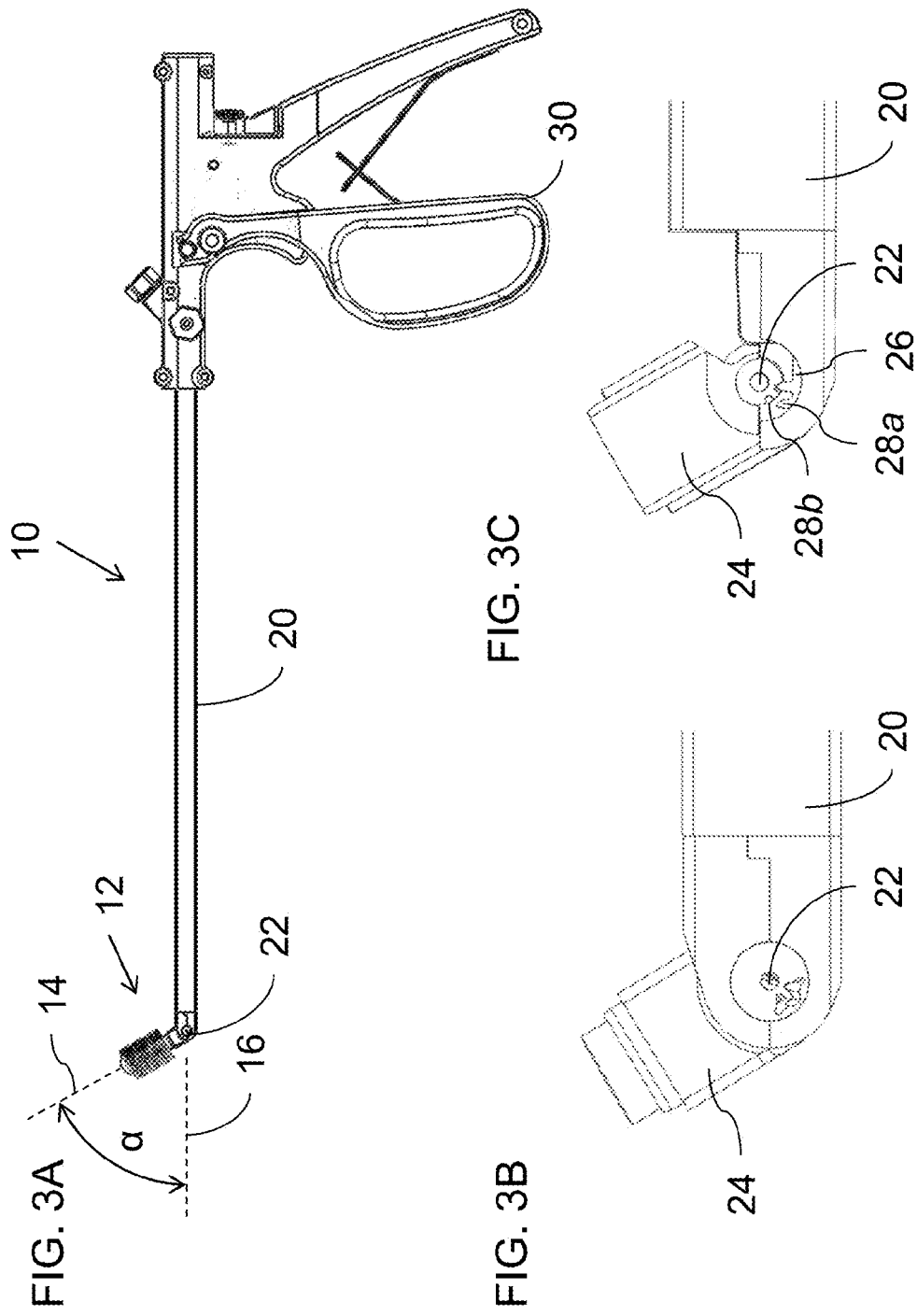

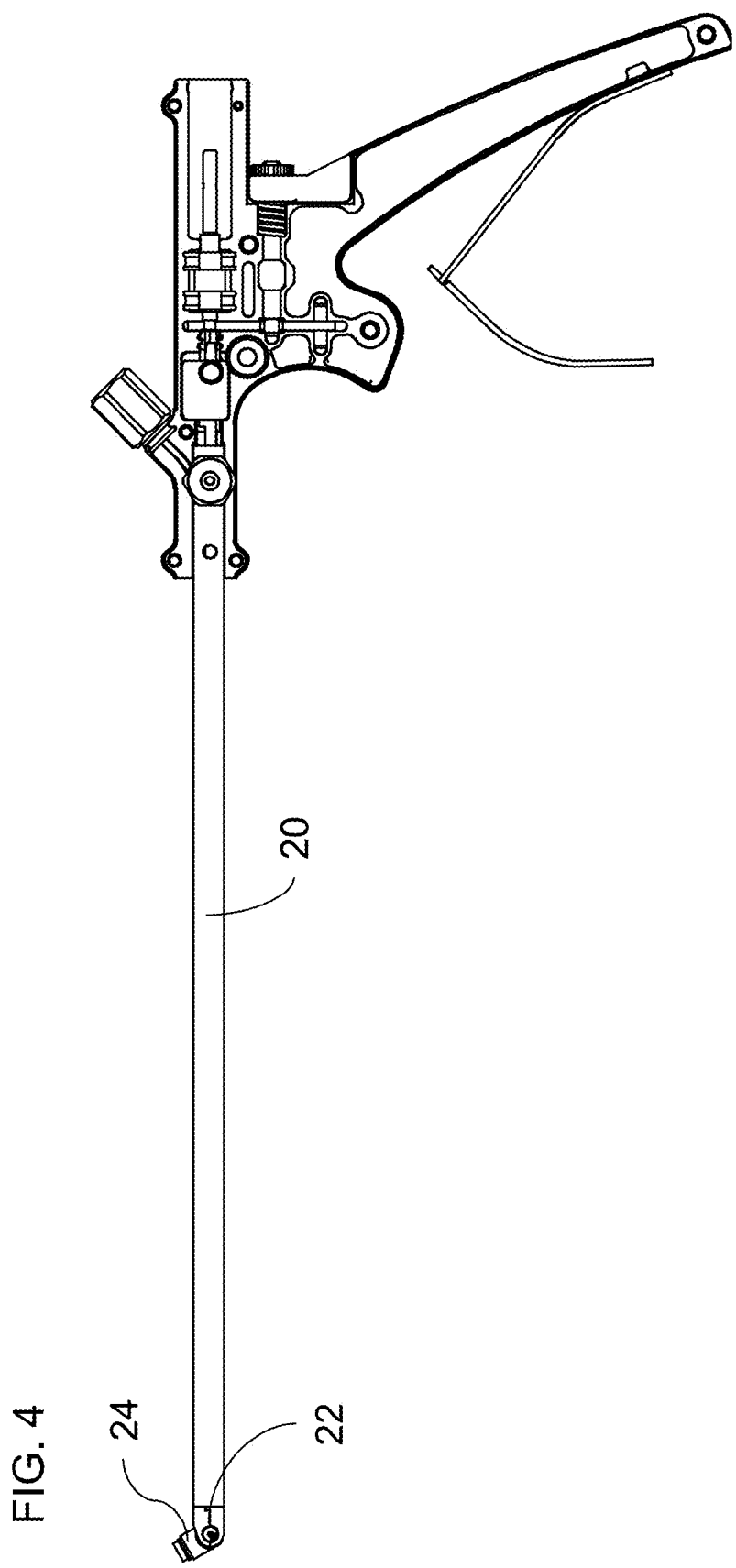

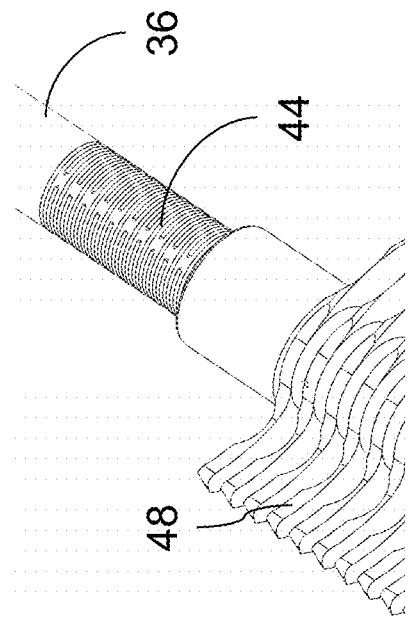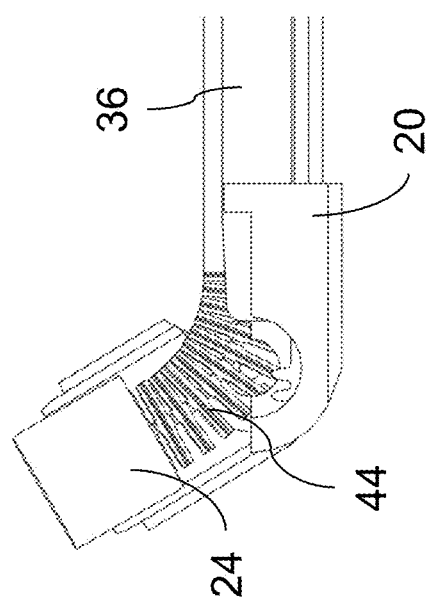
FIG. 5A
FIG. 5B

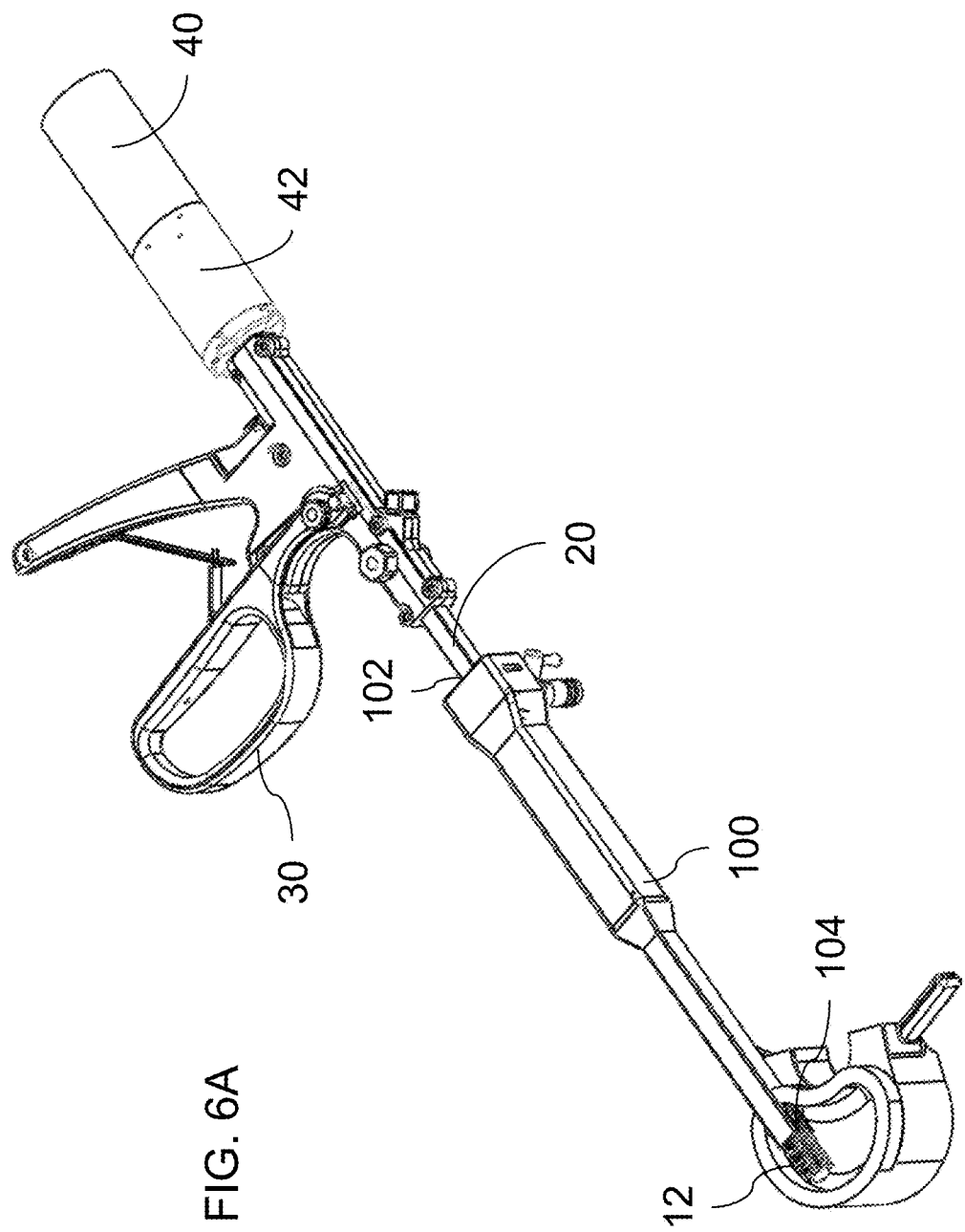

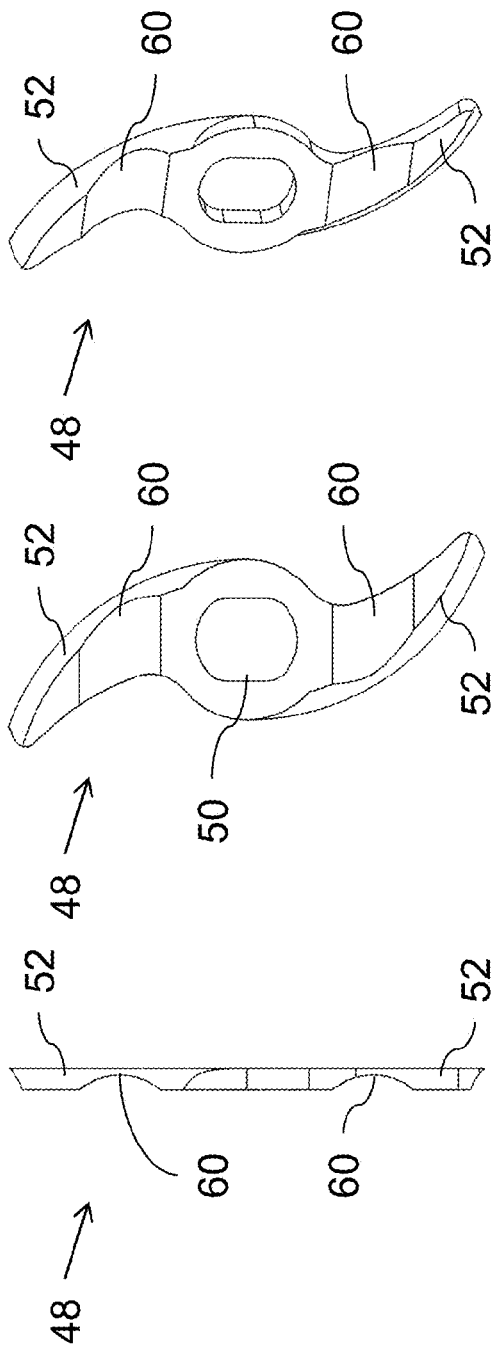

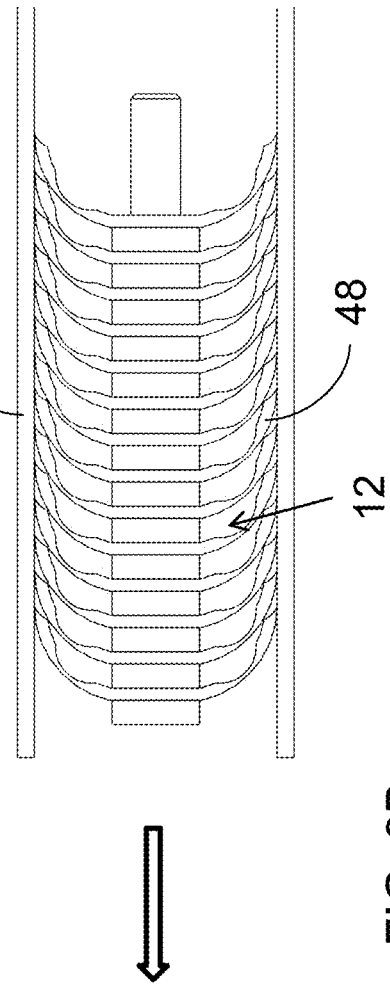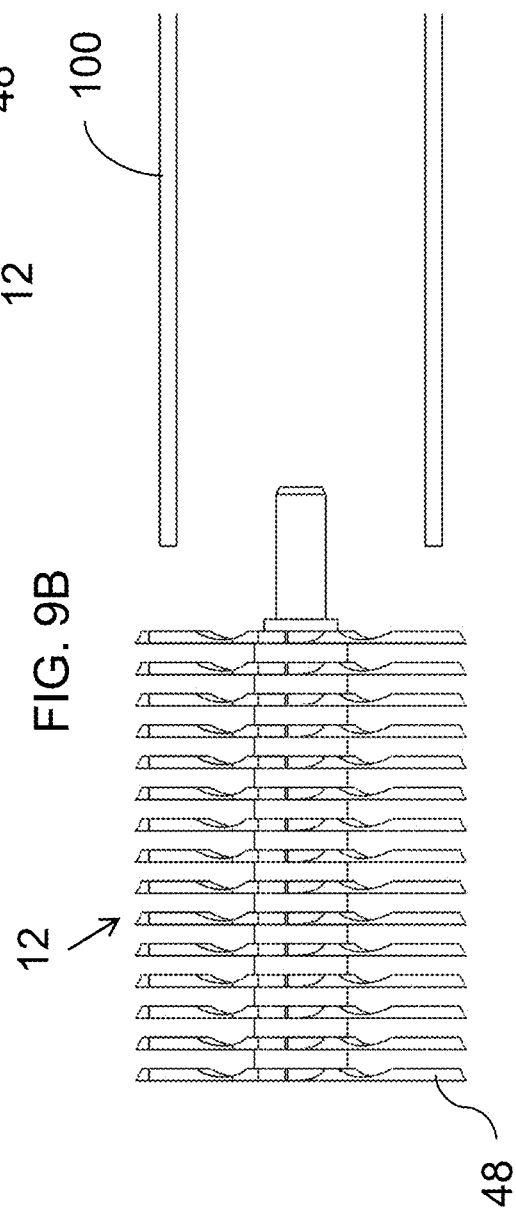
FIG. 9A
FIG. 9B

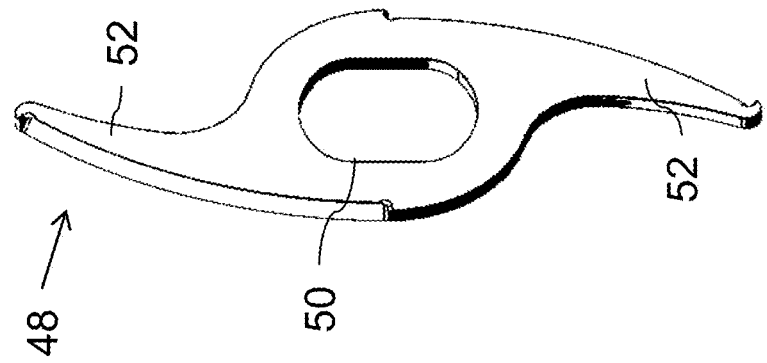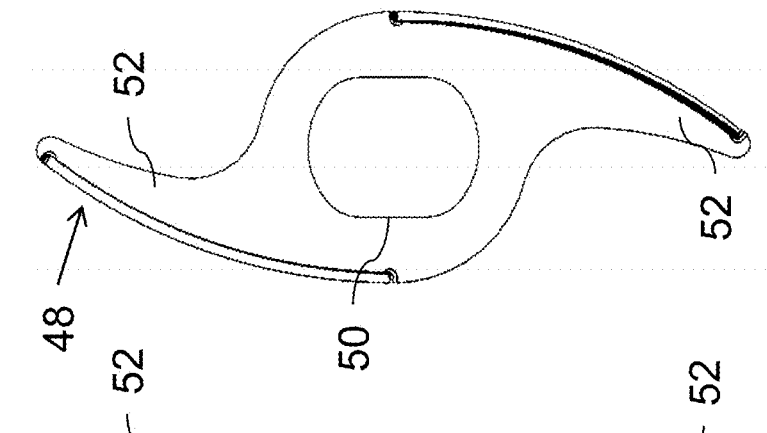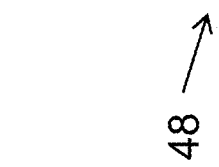

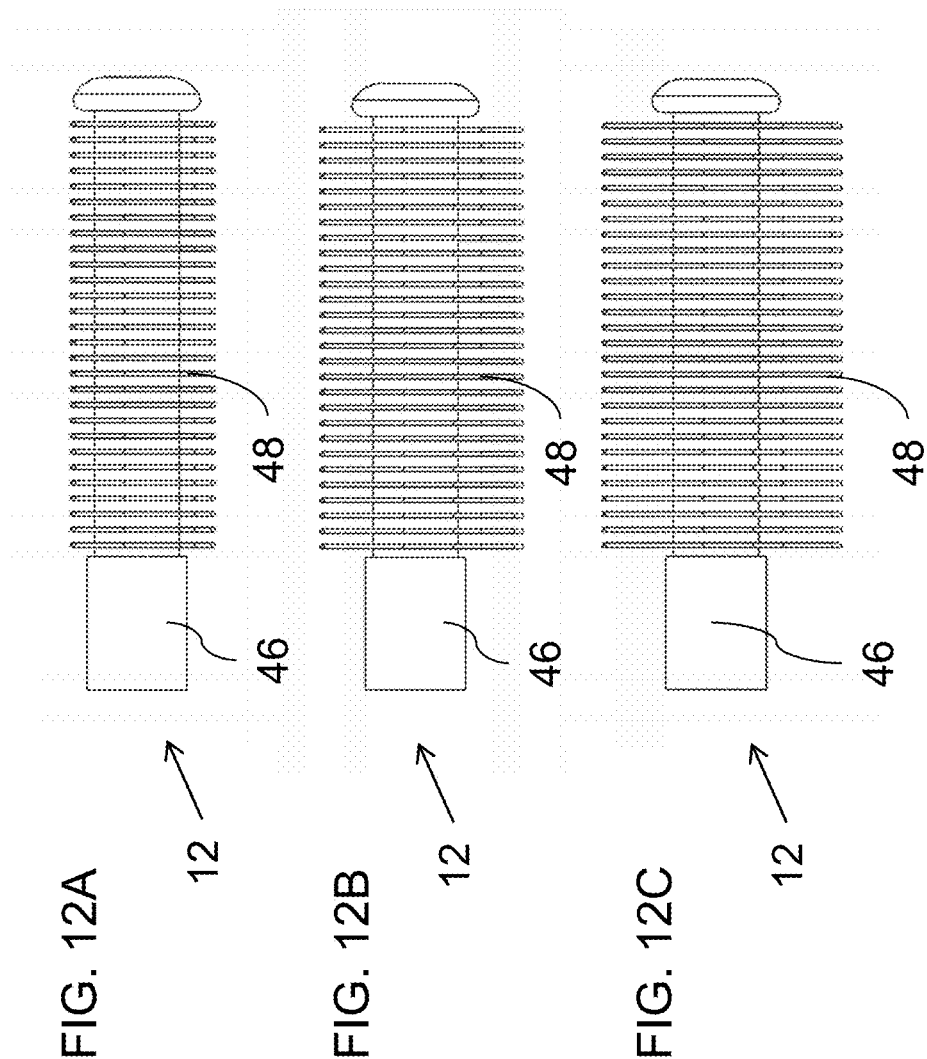

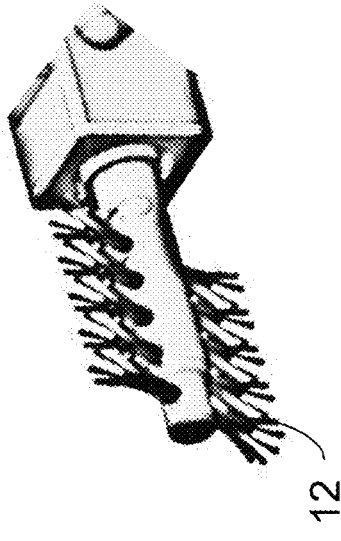
FIG. 18A
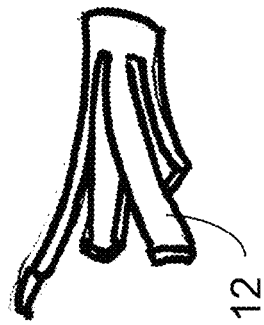
FIG. 18B
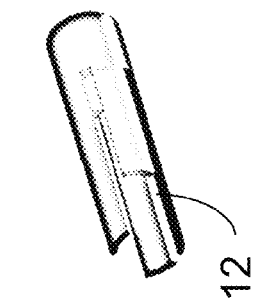
FIG. 19A
FIG. 19B
FIG. 20
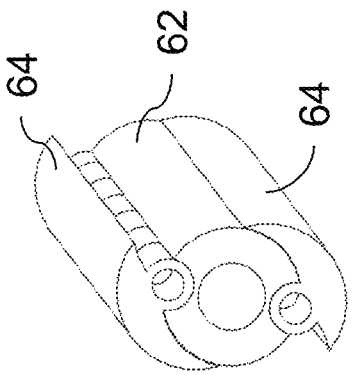
FIG. 21
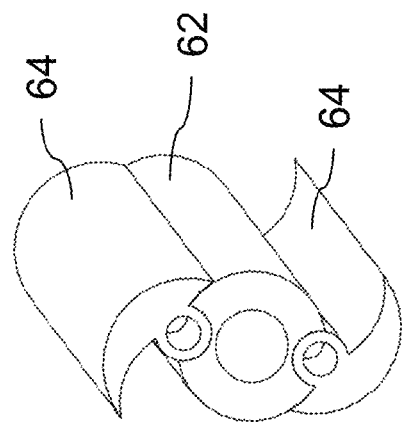

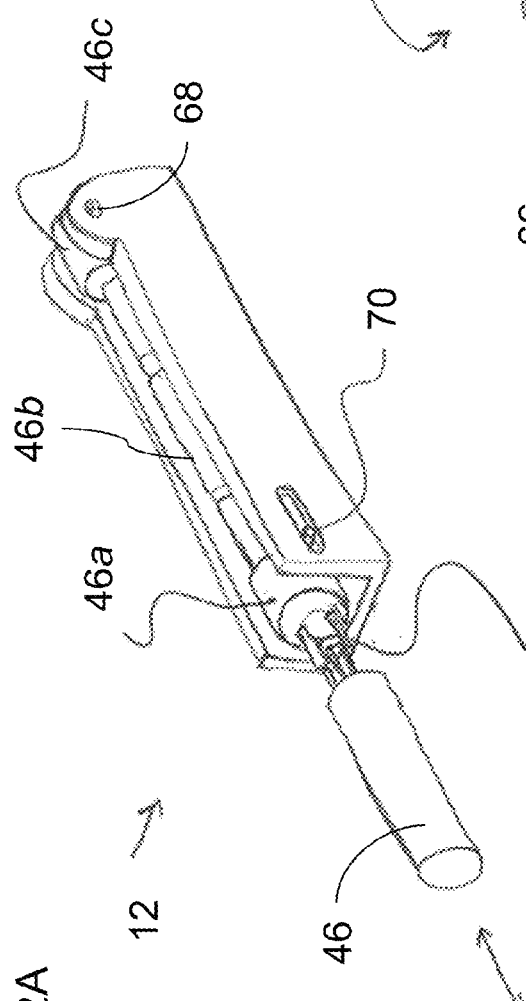
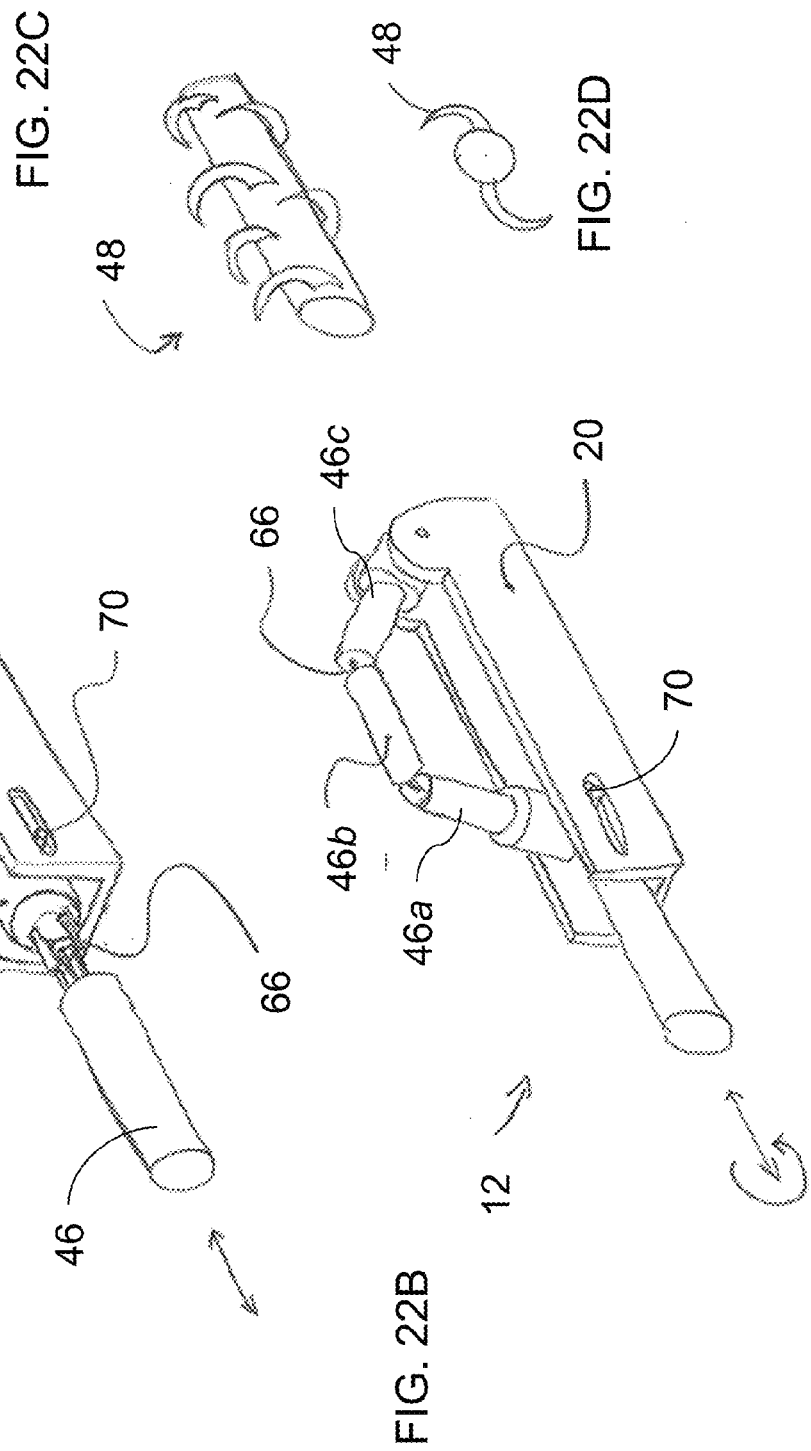
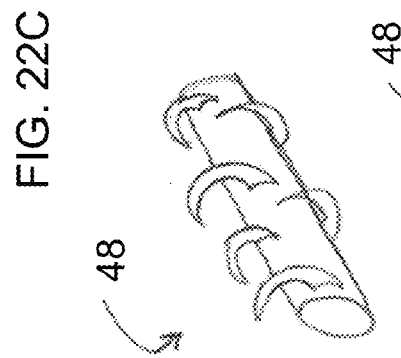
FIG. 22C
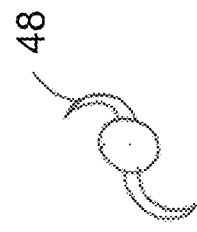
FIG. 22D
FIG. 22A
FIG. 22B

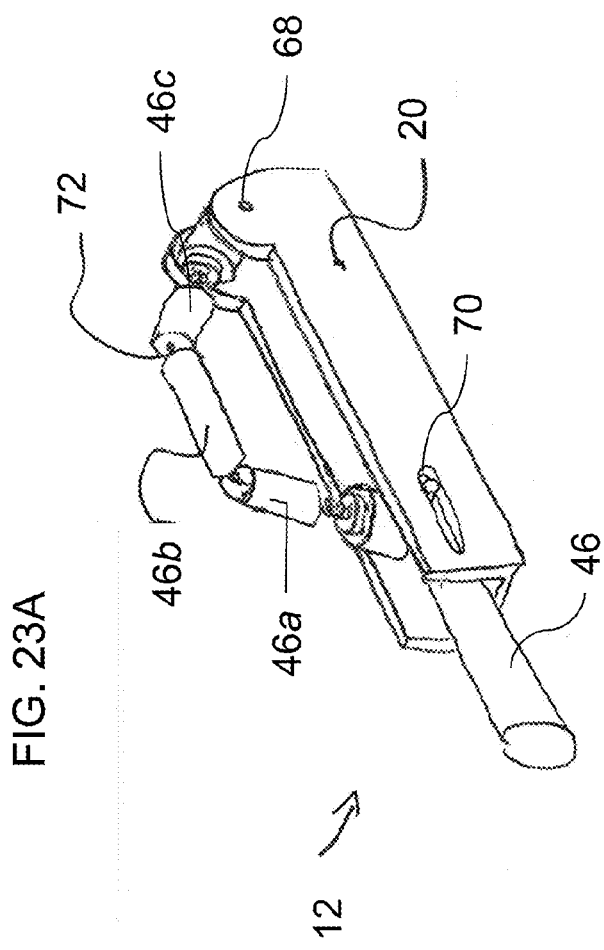
FIG. 23A
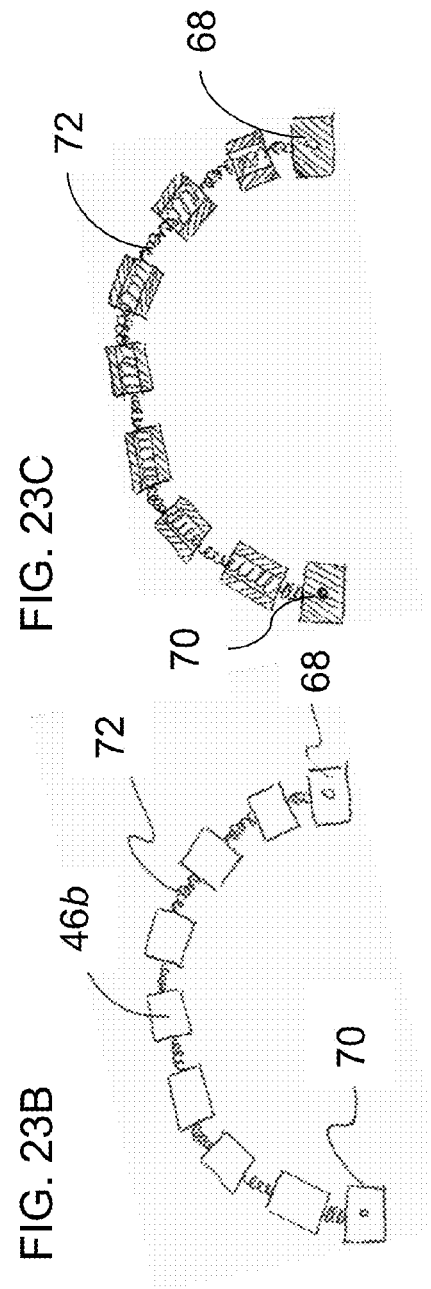
FIG. 23B
FIG. 23C

TISSUE DISRUPTION DEVICE AND CORRESPONDING METHODS

FIELD AND BACKGROUND OF THE INVENTION

The present invention relates to one or more devices configured to cut, grind or otherwise disrupt soft or hard tissue in a human or animal body, typically to facilitate removal of the tissue.

It is known to use various tools to disrupt tissue within the body. Examples of documents which may provide background for the present invention include U.S. Pat. Nos. 7,083,623, 7,500,977, 7,578,820, 7,914,534 and US Pre-Grant Patent Application Publication Nos. 2005/0203527, 2006/0264957, 2010/0030216 and 2010/0161060.

SUMMARY OF THE INVENTION

The present invention is a tissue disruption device and corresponding method.

According to an embodiment of the teachings of the present invention there is provided, a tissue disruption device for deployment via a rigid conduit having an open proximal end, a distal opening and a direction of elongation, the tissue disruption device comprising: (a) a rotary tissue disruptor having an axis of rotation, the rotary tissue disruptor being configured for insertion along the rigid conduit with the axis of rotation parallel to the direction of elongation; (b) an angular displacement mechanism associated with the rotary tissue disruptor and configured to selectively displace the rotary tissue disruptor such that the axis of rotation sweeps through a range of angular motion; and (c) a rotary drive linked to the rotary tissue disruptor so as to drive the rotary tissue disruptor in rotary motion while the rotary tissue disruptor is at a range of angular positions within the range of angular motion.

According to a further feature of an embodiment of the present invention, the angular displacement mechanism generates angular motion of the rotary tissue disruptor within a plane including the direction of elongation of the conduit.

According to a further feature of an embodiment of the present invention, the angular displacement mechanism generates angular motion that is asymmetric relative to the direction of elongation of the conduit.

According to a further feature of an embodiment of the present invention, the angular displacement mechanism generates angular motion of the rotary tissue disruptor through an angle of at least 30 degrees.

According to a further feature of an embodiment of the present invention, the angular displacement mechanism generates angular motion of the rotary tissue disruptor through an angle of at least 45 degrees.

According to a further feature of an embodiment of the present invention, the angular displacement mechanism includes a pivotal linkage at least partially defining a path of the angular motion.

According to a further feature of an embodiment of the present invention, there is also provided an elongated member deployable so as to extend through the conduit and linked so as to support the rotary tissue disruptor during the angular motion, and wherein the angular displacement mechanism includes an elongated actuator deployable so as to extend along the conduit and linked to the rotary tissue disruptor such that relative displacement of the elongated actuator and the elongated member actuates the angular motion of the rotary tissue disruptor.

According to a further feature of an embodiment of the present invention, the elongated actuator is a rotary drive shaft linking the rotary drive to the rotary tissue disruptor.

According to a further feature of an embodiment of the present invention, there is also provided a rotary drive shaft deployable so as to extend through the conduit and linking the rotary drive to the rotary tissue disruptor.

According to a further feature of an embodiment of the present invention, the rotary drive comprises at least one miniature motor deployed in proximity to the rotary tissue disruptor for insertion along the conduit.

According to a further feature of an embodiment of the present invention, the rotary drive comprises at least one miniature motor integrated with the rotary tissue disruptor so as to undergo angular motion together with the rotary tissue disruptor.

There is also provided according to an embodiment of the present invention, a tissue disruption system comprising: (a) the aforementioned tissue disruption device; and (b) a rigid conduit for receiving the tissue disruption device, the rigid conduit having an open proximal end and a distal opening.

According to a further feature of an embodiment of the present invention, there is also provided an elongated member deployable so as to extend through the conduit and linked so as to support the rotary tissue disruptor during insertion of the rotary tissue disruptor along the conduit, and wherein at least one of the rotary tissue disruptor and the elongated member mechanically interacts with the conduit such that linear displacement of the rotary tissue disruptor parallel to the direction of elongation is limited to a predefined range of displacement during the angular motion.

According to a further feature of an embodiment of the present invention, there is also provided an elongated member extending through the conduit and linked so as to support the rotary tissue disruptor during insertion of the rotary tissue disruptor along the conduit, and wherein at least one of the rotary tissue disruptor and the elongated member mechanically interacts with the conduit such that linear displacement of the rotary tissue disruptor parallel to the direction of elongation is prevented during the angular motion.

According to a further feature of an embodiment of the present invention, the distal opening includes an open tip of the conduit.

According to a further feature of an embodiment of the present invention, a distal tip of the conduit is closed, and wherein the distal opening is implemented as a lateral opening proximal to the distal tip.

According to a further feature of an embodiment of the present invention, the rotary tissue disruptor comprises a rotating shaft located on the axis of rotation and a plurality of blades projecting radially from, and spaced along, the shaft.

According to a further feature of an embodiment of the present invention, the plurality of blades include at least a first blade having a first radial length and at least a second blade having a second radial length smaller than the first radial length.

According to a further feature of an embodiment of the present invention, the plurality of blades include blades of differing radial lengths arranged such that an intermediate region along a length of the rotating shaft has blades of a first radial length and regions distal and proximal to the intermediate region have blades of a second radial length smaller than the first radial length.

According to a further feature of an embodiment of the present invention configured for insertion along a conduit having a given maximum internal dimension, the plurality of blades span a dimension perpendicular to the axis of rotation greater than the given maximum internal dimension, at least a subset of the blades being formed with a predefined flexion region configured to allow flexing of a part of the blades for insertion along the conduit.

According to a further feature of an embodiment of the present invention, the rotating shaft terminates in a rounded non-cutting tip.

According to a further feature of an embodiment of the present invention, at least one of the plurality of blades comprises: (a) a base portion mounted for rotation together with the rotating shaft; (b) a pivotal portion pivotally mounted relative to the base portion so as to be displaceable between a folded position folded towards the rotating shaft and a cutting position extended away from the rotating shaft; and (c) a biasing element deployed to bias the pivotal portion towards the folded position such that, during rotation of the rotating shaft, the blade opens under the effect of centripetal force to the cutting position and, when stopped, the blade is biased towards the folded position.

According to a further feature of an embodiment of the present invention, the rotary tissue disruptor comprises a plurality of rotating segments flexibly interlinked so as to rotate together, and wherein the axis of rotation is the axis of rotation of a first of the segments.

According to a further feature of an embodiment of the present invention, a distal segment of the rotary tissue disruptor is pivotally anchored to a support element such that the angular motion occurs as an arching motion of the plurality of segments.

There is also provided according to an embodiment of the present invention, a method for disrupting target tissue in a human or animal body, the method comprising the steps of (a) introducing a rigid conduit into the body, the conduit having an open proximal end and a distal opening, the conduit being fixed in a position with the distal opening adjacent to the target tissue; (b) introducing through the rigid conduit the aforementioned tissue disruption device so that at least part of the rotary tissue disruptor projects from the distal opening; and (c) actuating both the rotary drive and the angular displacement mechanism so that the rotary tissue disruptor rotates at a plurality of positions within the range of angular motion, thereby disrupting the target tissue.

According to a further feature of an embodiment of the present invention, the target tissue includes at least part of an intervertebral disc.

According to a further feature of an embodiment of the present invention, the target tissue is soft tissue.

According to a further feature of an embodiment of the present invention, the target tissue is bone.

According to a further feature of an embodiment of the present invention, the target tissue is hard tissue.

According to a further feature of an embodiment of the present invention, the target tissue is a tumor.

According to a further feature of an embodiment of the present invention, at least part of the target tissue is removed by application of suction via the rigid conduit.

According to a further feature of an embodiment of the present invention, at least part of the target tissue is removed through removal of the rotary tissue disruptor with a quantity of the target tissue lodged therein.

BRIEF DESCRIPTION OF THE DRAWINGS

The invention is herein described, by way of example only, with reference to the accompanying drawings, wherein:

FIG. 1A is an isometric view of a tissue disruption device, constructed and operative according to an embodiment of the present invention, shown with an end portion in a first angular position;

FIG. 1B is an enlarged view of the end portion of the device of FIG. 1A;

FIG. 2A is an isometric view of the device of FIG. 1A shown with the end portion in a second angular position;

FIG. 2B is an enlarged view of the end portion of the device of FIG. 2A;

FIG. 3A is a side view of the device as illustrated in FIG. 2A;

FIGS. 3B and 3C are enlarged side and cut-away views of a pivotal axis from the end portion of the device of FIG. 3A;

FIG. 4 is a partially disassembled view of the device of FIG. 3A showing the inner structure of a handle portion of the device;

FIG. 5A is a partially cut-away view of the region of the pivotal axis of FIGS. 3B and 3C, showing a flexing region of a rotary drive shaft;

FIG. 5B is an enlarged isometric view of the flexing region of FIG. 5A;

FIGS. 6A and 6B are schematic isometric views of the device of FIG. 1A in use inserted via a conduit to perform at least part of a discectomy, the device being shown with the end portion in first and second angular positions, respectively;

FIGS. 8A-8C are side, front and isometric views, respectively, of a blade for use in the rotary tissue disruptor of an embodiment of the present invention, the blade including flexion regions;

FIGS. 8D and 8E are isometric and side views, respectively, illustrating a rotary tissue disruptor assembled from a plurality of the blades of FIGS. 8A-8C mounted on a rotating shaft;

FIGS. 9A and 9B are schematic side views illustrating the insertion of the rotary tissue disruptor of FIG. 8D along a conduit and the recovery of a transverse dimension of the disruptor after emerging from the conduit, respectively;

FIGS. 10A-10C are side, front and isometric views, respectively, of a further example of a blade for use in the rotary tissue disruptor of an embodiment of the present invention;

FIGS. 12A-12C are schematic side views of rotary tissue disruptors having sequentially increasing dimensions, for use in procedures according to teachings of an aspect of the present invention;

FIGS. 18A and 18B are schematic illustrations of an alternative form of a cutting element for use in embodiments of the present invention, shown in a compacted state and a deployed state, respectively;

FIGS. 19A and 19B are schematic illustrations of an alternative form of a cutting element for use in embodiments of the present invention, shown in a compacted state and a deployed state, respectively;

FIG. 20 is a schematic illustration of an alternative form of a cutting element for use in embodiments of the present invention;

FIG. 21 is a schematic illustration of an alternative form of a cutting element for use in embodiments of the present invention;

FIGS. 22A and 22B are schematic isometric views of an alternative implementation of a rotary tissue disruptor including a plurality of rotary segments in a straightened form and an arched form, respectively;

FIGS. 22C and 22D are schematic isometric and end views, respectively, of an implementation of a segment from the rotary tissue disruptor of FIG. 22A;

FIG. 23A is a schematic isometric view of a rotary tissue disruptor similar to that of FIG. 22B but employing segments mounted on a common flexible shaft;

FIGS. 23B and 23C are schematic side and cross-sectional views illustrating the mounting of segments on a common flexible shaft according to the principles of FIG. 23A.

DESCRIPTION OF THE PREFERRED EMBODIMENTS

Figure 6B:
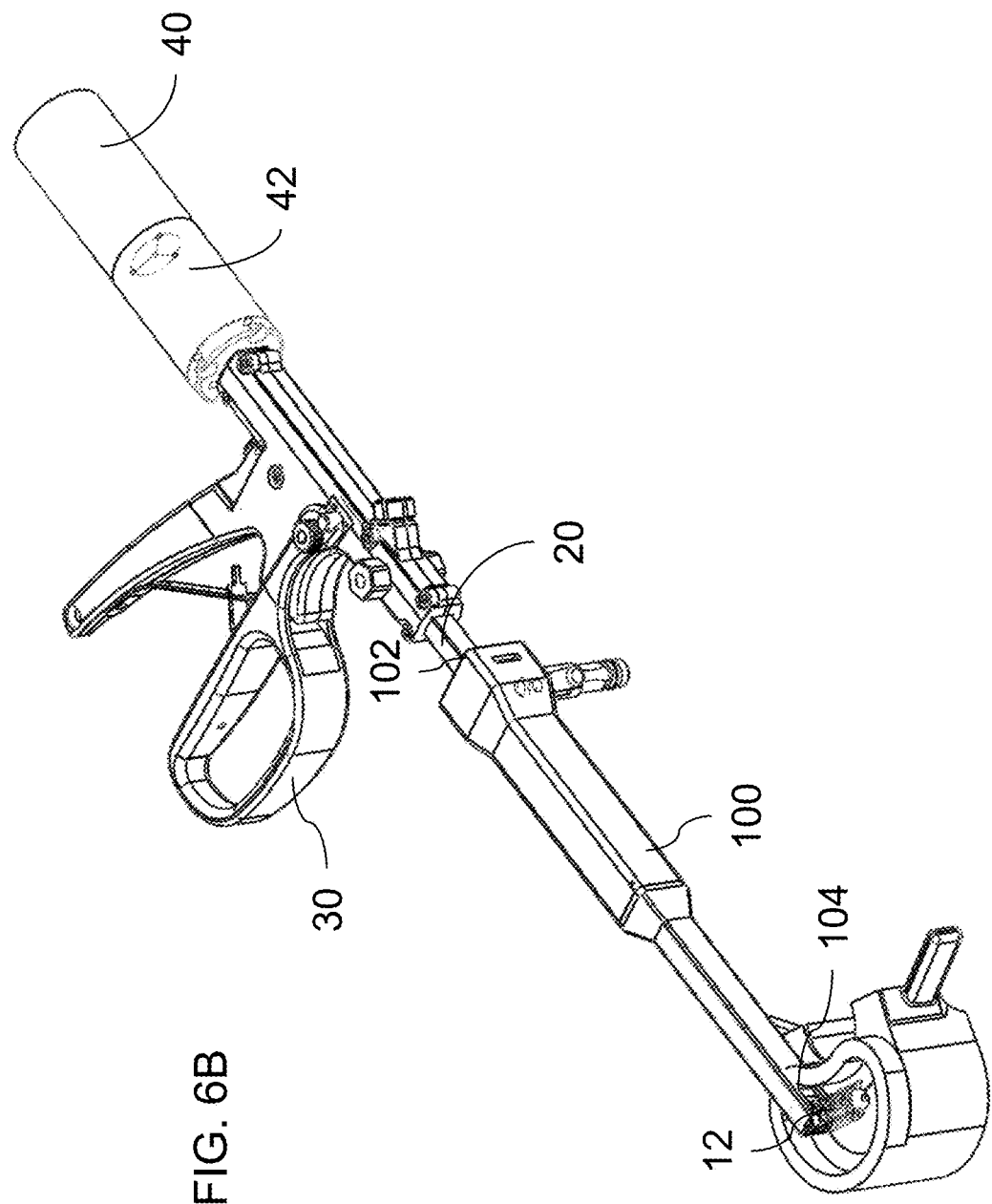

The present invention is a tissue disruption device and corresponding method.

A preferred embodiment is particularly configured for cutting and grinding intervertebral disc material during discectomy or fusion procedures in the cervical, thoracic and lumbar spine The principles and operation of devices and methods according to the present invention may be better understood with reference to the drawings and the accompanying description.

Referring now generically to the drawings, there is shown a tissue disruption device, generally designated 10, for deployment via a rigid conduit 100 (FIGS. 6A and 6B) having an open proximal end 102 and a distal opening 104. The term "distal opening" in this context denotes an opening which is either at the tip of the conduit, or in the case of a lateral opening, which is sufficiently near the distal end of the conduit to provide allow tissue disruption device 10 to disrupt tissue adjacent to the distal end of the conduit.

In general terms, tissue disruption device 10 includes a rotary tissue disruptor 12 having an axis of rotation 14. Rotary tissue disruptor 12 is configured for insertion along the rigid conduit with its axis of rotation 14 parallel to an insertion direction 16, corresponding to the direction of elongation of the conduit. An angular displacement mechanism is configured to selectively displace rotary tissue disruptor 12 such that axis of rotation 14 sweeps through a range of angular motion α (FIG. 3A). A rotary drive is linked to rotary tissue disruptor 12 so as to drive the rotary tissue disruptor in rotary motion about axis 14 while the rotary tissue disruptor is at a range of angular position within the range of angular motion.

As illustrated in the accompanying drawings, the angular displacement mechanism preferably generates angular motion of rotary tissue disruptor 12 within a plane that includes insertion direction 16, and preferably in a motion that is asymmetric relative to insertion direction 16. In the preferred implementations illustrated here, the range of motion is from the straight insertion state in which axis of rotation 14 is parallel to the insertion direction 16 and a deflected state in which axis 14 is inclined by angle α relative to the insertion direction 16. In certain preferred implementations, the range of deflection α is at least 30 degrees, and in some cases at least 45 degrees.

The positioning and orientation of rotary tissue disruptor 12 is preferably delineated by the conduit position such that careful alignment of the conduit is sufficient to ensure that target outside the region of target tissue cannot be accidentally damaged by operation of the rotary tissue disruptor. In the case of a purely lateral distal opening in the conduit, the nature of the angular motion together with the distal and proximal ends of the opening inherently delimit the region of operation of the tissue disruptor 12. Where the distal opening includes an open distal tip of the conduit, the tissue disruption device 10 and conduit 100 preferably include complementary abutment features (not shown) which define a fully inserted position, thereby preventing incursion of the rotary tissue disruptor 12 beyond the target tissue at a given depth beyond the conduit tip.

Structurally, rotary tissue disruptor 12 is preferably supported by an elongated member 20 deployable so as to extend through the conduit. Either rotary tissue disruptor 12 or elongated member 20 preferably mechanically interacts with conduit 100 such that linear displacement of the rotary tissue disruptor parallel to the direction of elongation is limited to a predefined range of displacement during the angular motion. In other preferred implementations, linear displacement of rotary tissue disruptor 12 parallel to the direction of insertion is substantially prevented during the angular motion. As also seen in FIGS. 6A and 6B, at least part of conduit 100 has a non-circular cross-section with at least one flat side, most preferably, a rectangular cross-section. Similarly, at least part of elongated member 20 has a non-circular cross-section with a corresponding at least one flat side, and most preferably, a rectangular cross-section. Engagement of elongated member 20 within conduit 100 thus limits angular motion of said tissue disruption device about the direction of elongation of the conduit.

As a further precaution against unintended penetration beyond the desired target tissue, in certain implementations, the tip of tissue disruptor 12 terminates in a rounded non-cutting tip 18.

Turning now to the angular displacement mechanism, as mentioned, this is configured to selectively displace rotary tissue disruptor 12 such that axis of rotation 14 sweeps through a range of angular motion α. The phrase "sweep through" is used in this context to refer to the motion caused by pivoting about a location near or beyond one end of the tool, or any other motion in which the tool's axis of rotation over most or all of the length of the rotating body advances in the same general direction, even if with variable magnitude, so as to sweep out an area in which the tissue is to be disrupted. This motion is suited to the various implementations of the rotary tissue disruptor presented herein, in which the cutting or disrupting of tissue occurs primarily, if not exclusively, as the disruptor advances laterally through tissue, i.e., in a direction significantly non-parallel with the axis of rotation of the rotary tissue disruptor.

In certain particularly preferred implementations, the angular displacement mechanism includes a pivotal linkage at least partially defining a path of the angular motion. The pivotal linkage may be implemented as a pivot pin sliding in a slot, a hinge, or any other mechanical engagement which defines a pivotal engagement. FIGS. 1A-7C illustrate an implementation in which rotary tissue disruptor 12 is mounted to elongated member 20 at a fixed hinge 22 which supports a base block 24 of the disruptor.

In order to achieve controlled displacement of tissue disruptor 12 within its range of motion, the angular displacement mechanism preferably uses a positive displacement mechanism, meaning that motion of an actuating member forces a corresponding motion of tissue disruptor 12, in contrast to relying upon resilient biasing. Most preferably, the angular displacement mechanism employs a rigid linkage to actuate the displacement.

Thus, by way of one non-limiting example, as best seen in FIGS. 3A and 3C, tissue disrupting device 10 here includes an elongated actuator 26 extend along alongside, or in this case within, elongated member 20, and linked to tissue disruptor 12 such that relative displacement of elongated actuator 26 and elongated member 20 actuates the angular motion of rotary tissue disruptor 12. In the implementation illustrated here, actuator 26 is located on the side of hinge 22 away from the direction of deflection such that advancing of actuator 26 distally causes increased deflection of axis of rotation 14 from direction of insertion 16 while retraction in a proximal direction returns disruptor 12 towards its straightened state. FIG. 3C shows the use of toothed engagement to allow transfer of significant torque to the angular displacement of disrupter 12, with teeth 28*a* near the end of actuator 26 engaged in corresponding teeth/recesses 28*b* formed as part of base block 24. A manually operated handle grip 30 is linked so as to advance actuator 26 when squeezed and to retract actuator 26 when released.

Figure 14A:
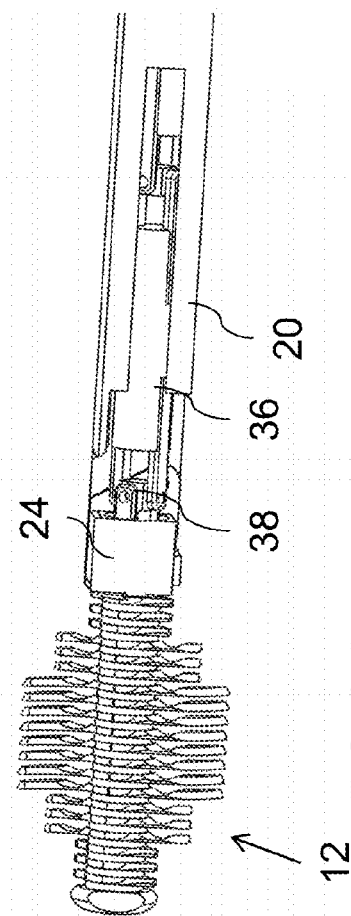
FIGS. 14A and 14B are schematic illustrations of an end portion of a tissue disruption device according to an embodiment of the present invention illustrating a further angular displacement mechanism in an insertion state and a deflected state, respectively.
Figure 14B:
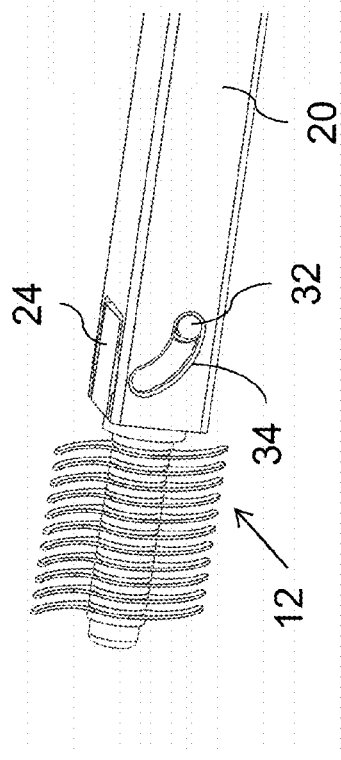

Referring here briefly to FIGS. 14A-14B and 15A-15B, these illustrate alternative non-limiting examples of angular deflection mechanisms according to the present invention. In the case of FIGS. 14A and 14B, a pin 32 projecting from each side of base block 24 is engaged in an arcuate slot 34 formed in elongated member 20. Arcuate slot 34 is configured such that, when block 24 is advanced relative to elongated member 20, pin 32 rides along slot 34 to generate deflection as illustrated in FIG. 14B. Advancing of base block 24 may be achieved either by a dedicated actuator element as described above or by applying longitudinal force to a torsion drive shaft passing along the elongated body.

Figure 15A:
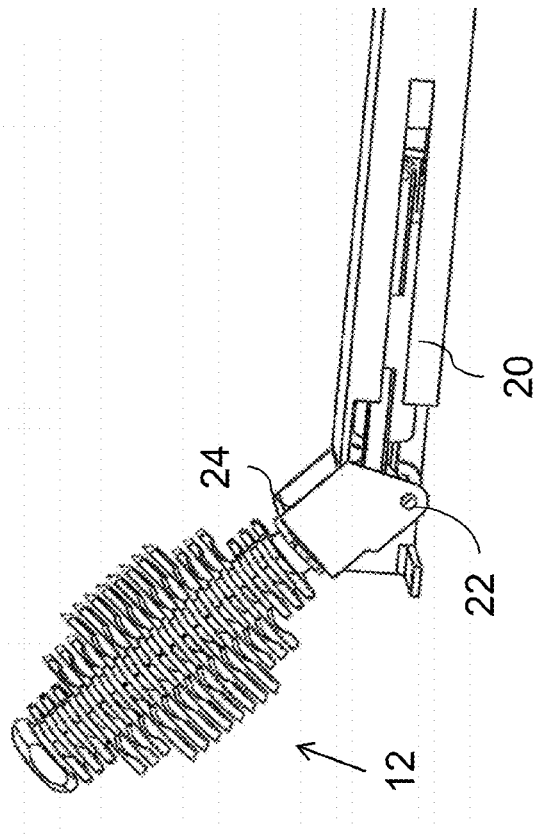
FIGS. 15A and 15B are schematic illustrations of an end portion of a tissue disruption device according to an embodiment of the present invention illustrating a further angular displacement mechanism in an insertion state and a deflected state, respectively.
Figure 15B:
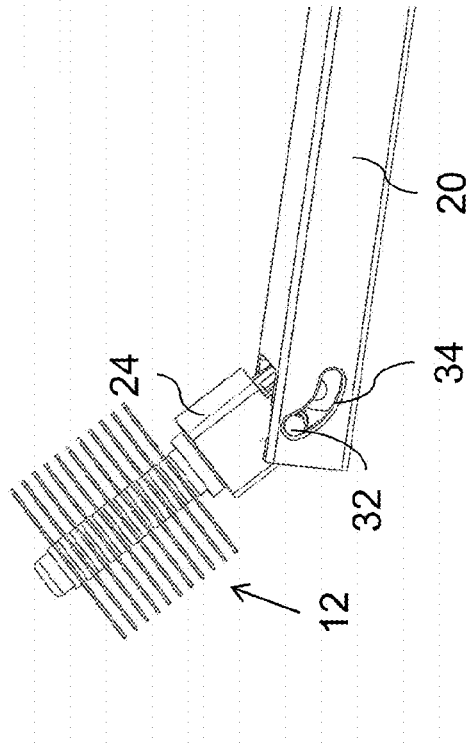
Figure 16D:
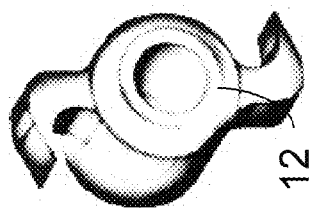
FIGS. 16A-16E are schematic illustrations of alternative forms of cutting elements for use in embodiments of the present invention.
Figure 16C:
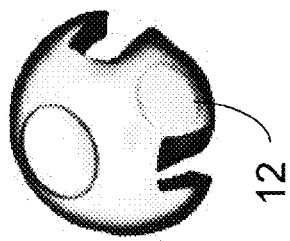
Figure 16B:
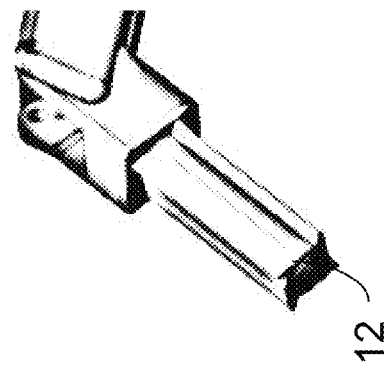
Figure 16A:
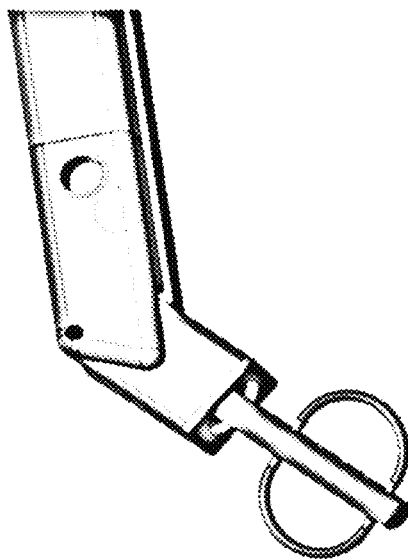
Figure 16E:
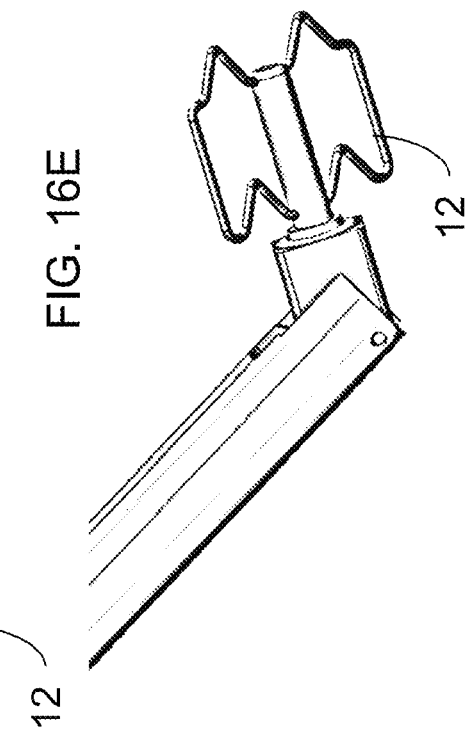
Figure 17B:
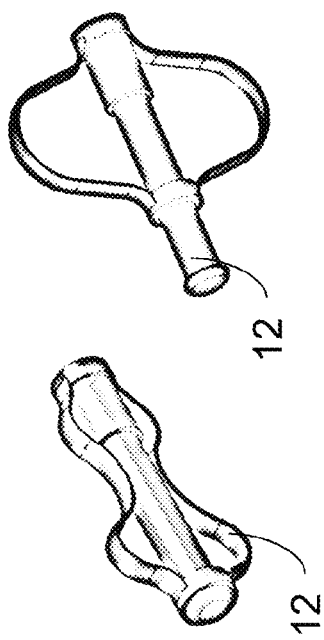
FIGS. 17A and 17B are schematic illustrations of an alternative form of a cutting element for use in embodiments of the present invention, shown in a compacted state and a deployed state, respectively.
Figure 17A:
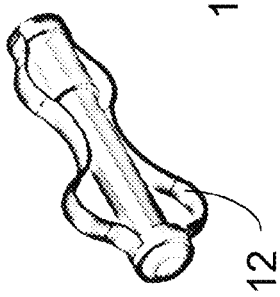

Turning to FIGS. 15A and 15B, these illustrate a case where a pivot hinge 22 is at one side of base block 24, such that rearward displacement of the torsion drive shaft causes angular displacement of rotary tissue disruptor 12. The cutaway view of FIG. 15A shows the torsion drive train, here including a rotary drive shaft 36 with a universal joint 38.

Turning now to details of the rotary drive of the present invention, as mentioned above, this is linked to rotary tissue disruptor 12 so as to drive the rotary tissue disruptor in rotary motion about axis 14 while the rotary tissue disruptor is at a range of angular position within the range of angular motion. Most preferably, one or more motor is used to provide the motive force to drive tissue disruptor 12. The motor may be electric, hydraulic or pneumatically driven, with the electric option typically preferred for reasons of convenience of implementation. Manually actuated rotary drive arrangements, for example, with a manually rotated power input handle, also fall within the scope of the present invention.

In a first set of implementations of the present invention, the rotary drive is located in the proximal portion of the device, outside the body, as exemplified by motor 40 and step-down gear 42 in FIGS. 6A and 6B. In this case, the output power it transferred along elongated member 20 by a rotary drive shaft 36, which must be configured to transfer rotary power to tissue disruptor 12 while accommodating the angular motion of the disruptor. In the example illustrated in FIGS. 5A and 5B, this is achieved by using a drive shaft 36 with an integrated flexion region 44 formed by a series of orthogonally cut slots. An alternative to this approach is the use of one or more flexible linkage, such as the aforementioned universal joint 38 illustrated in FIG. 15A.

As an alternative to this approach, alternative implementations of the present invention employ one or more miniature motor deployed in proximity to rotary tissue disruptor 12, i.e., near the distal end of the device 10, so that the motor is itself inserted along conduit 100 into the body. In a most preferred implementation of this approach, the miniature motor(s) are integrated within base block 24 or at any other location beyond the point of pivoting, thereby avoiding the need for a flexible linkage. The required electrical supply can readily be provided along the length of the elongated member 20 by use of flexible wires which accommodate the required motion.

Suitable miniature motors are commercially available from a number of sources, such as the product line "DC-Micromotors" available from Dr. Fritz Faulhaber GmbH (Germany), and rotary SQUIGGLE™ motors available from NewScale Technologies of Victor, N.Y. (USA). The required motor specifications can readily be chosen by one ordinarily skilled in the art according to the power, speed and maximum torque required for each given application. In some cases, a plurality of miniature motors may be connected in series to increase the total output power of the assembly.

Turning now to details of rotary tissue disruptor 12, it should be noted that this may be any type of rotating tool for disrupting tissue of any type. The term "disrupting" as used herein refers generically to any process which changes the state or properties of tissue by direct application of mechanical energy, including but not limited to, cutting, scoring, severing, slicing, lacerating, grinding and pulverizing. The tissue disruption may be performed on healthy or diseased tissue, whether hard tissue or soft tissue. For simplicity of terminology, the elements which directly perform the tissue disruption will be referred to herein as "blades" or "cutting elements", but depending upon the type of tissue and the type of disruption desired, these cutting elements may not be sharpened, and may in some cases be implemented as flexible or brush-like elements. Various non-limiting exemplary "cutting elements" will be illustrated herein. A suitable selection of cutting elements suitable for each particular application will readily be made by a person ordinarily skilled in the art on the basis of the examples described together with an understanding of each particular intended application.

In a first set of particularly preferred but non-limiting implementations, rotary tissue disruptor 12 is formed with a rotating shaft 46 located on axis of rotation 14 and a plurality of blades 48 projecting radially from, and spaced along, shaft 46. Examples of this type are illustrated herein in FIGS. 1A-15B.

Blades 48 may have many different forms. Two non-limiting but preferred examples are illustrated in FIGS. 8A-8C and FIGS. 10A-10C, respectively. In both cases, blades 48 have a shaped central opening 50 for non-rotatable mounting on shaft 46 and two diametrically opposed cutting portions 52. Although shown here with two cutting portions per blade, a single cutting portion per blade, or 3 or more cutting portions per blade, may also be used.

FIGS. 8D and 8E show a partially assembled tissue disruptor 12 formed from a number of the blades of FIGS. 8A-8C with interposed spacers 54. In this example, all of the blades are of equal dimensions and are equally spaced.

Figure 7A:
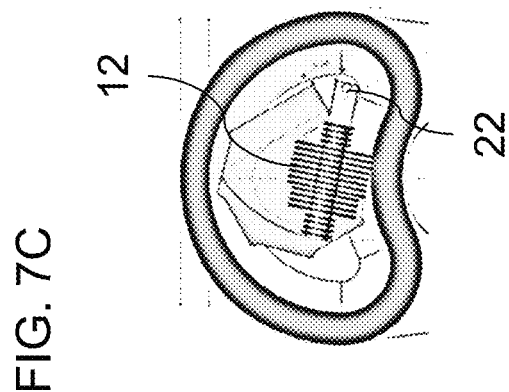
FIGS. 7A-7C are schematic plan views showing an area of the intervertebral disc swept through by a rotary tissue disruptor of the device of FIG. 6A.
Figure 7B:
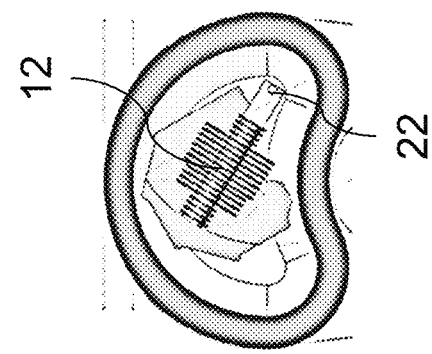
Figure 7C:
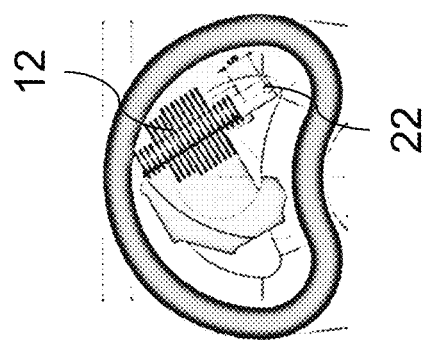
Figure 11B:
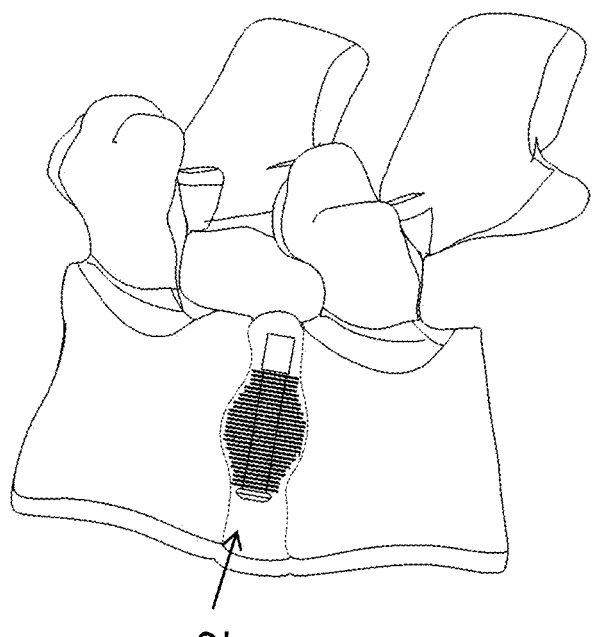
FIG. 11B is a schematic illustration of an application of the rotary tissue disruptor of FIG. 11A for discectomy and endplate preparation.
Figure 11A:
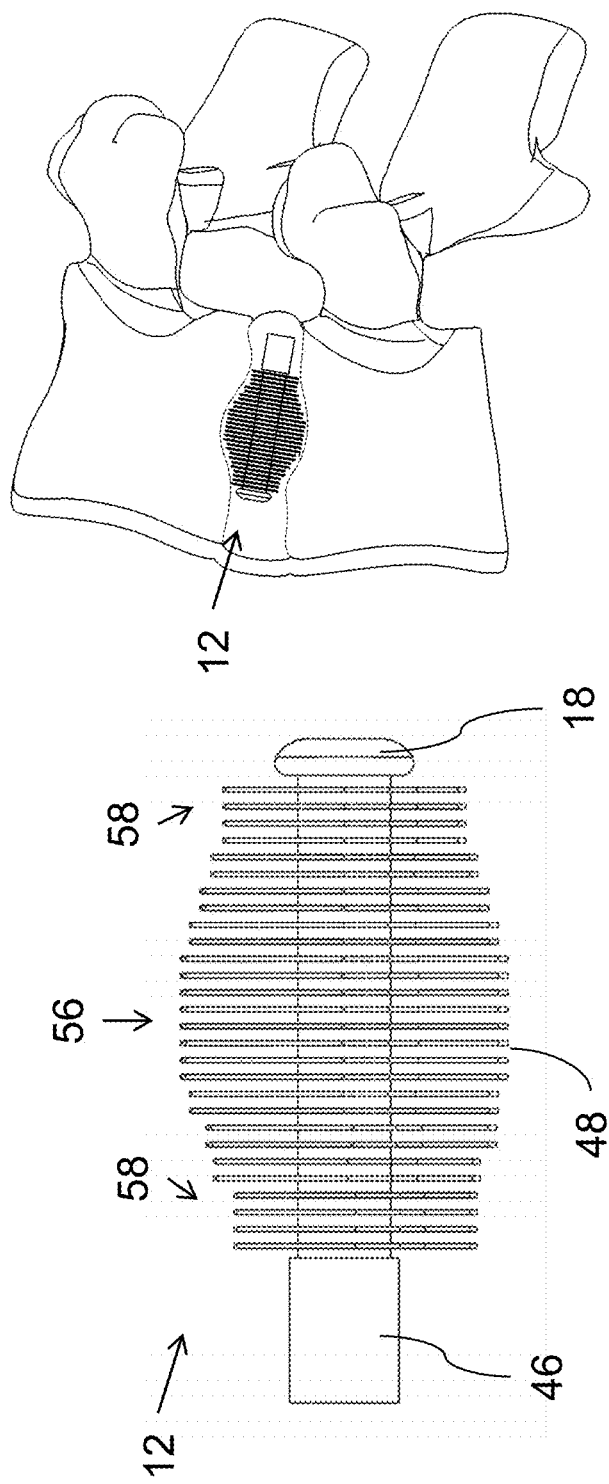
FIG. 11A is a schematic side view of a rotary tissue disruptor according to an embodiment of the present invention, employing graduated blade lengths.
Figure 13A:
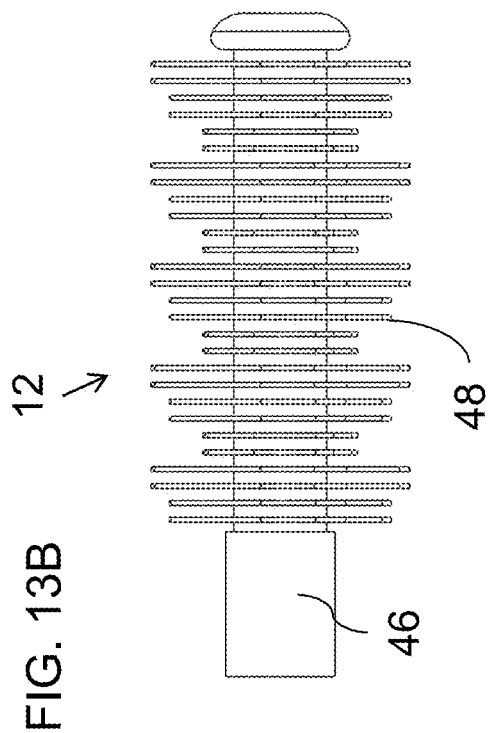
FIGS. 13A-13D are schematic side views of additional rotary tissue disruptors according to embodiments of the present invention, illustrating additional options for variable cutting element size, sequence and spacing.
Figure 13B:
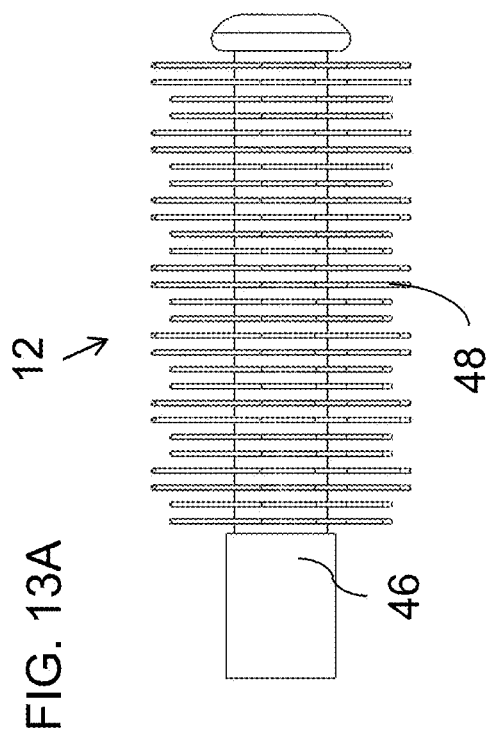
Figure 13C:
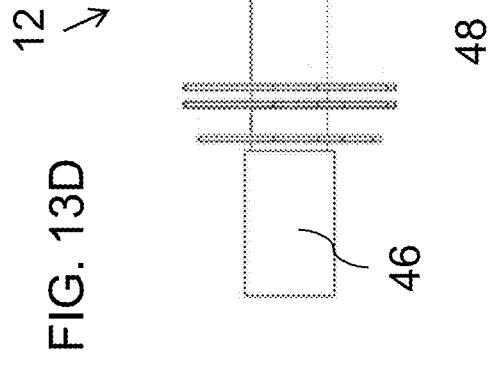
Figure 13D:
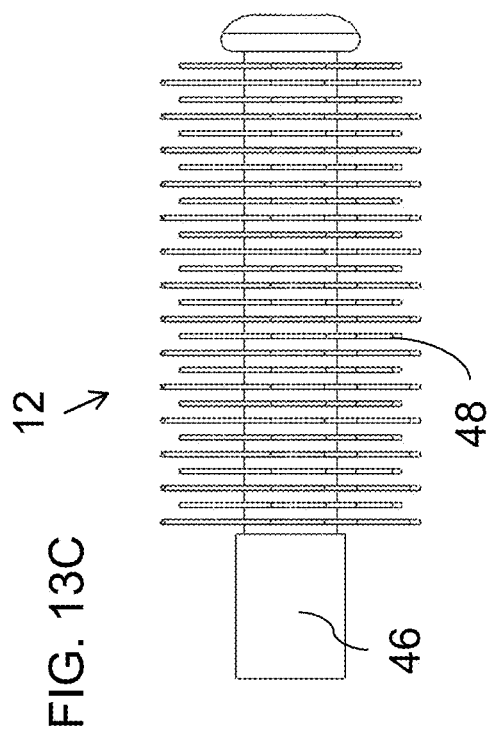

FIG. 11A illustrates a partially assembled tissue disruptor 12 which has different radial lengths of blades in different regions. The term "radial length" is used herein to refer to the maximum distance reached by any part of a blade from the axis of rotation. In the example illustrated here, an intermediate region 56 along a length of rotating shaft 46 has blades of a first radial length and regions 58 distal and proximal to the intermediate region have blades of a second radial length smaller than the first radial length. This configuration is particularly useful in certain applications, such as for example during a spinal fusion or disc replacement procedure. Specifically, this variable length profile is effective to break up intervertebral disc material as part of a discectomy procedure and at the same time penetrates more deeply in a central region, helping to bare "bleeding bone" for effective anchoring and integration of an implant. FIGS. 7A-7C illustrate the extent of coverage achieved using such a profile in an axial plane during discectomy.

FIGS. 12A-12C illustrate a set of uniform-length blades in three different sizes, which may be used sequentially to perform gradually increased tissue disruption. For this purpose, and to switch between any other variant implementations described herein, tissue distraction device 10 is preferably constructed to allow quick release and interchange of tissue disruptors 12 during a procedure. Quick release mechanisms of various types are known in the art, and will not be described here in detail.

FIGS. 13A-13D illustrate further variant implementations of varying radial length and spacing of blades 48. Variations in the lengths and density of the cutting elements can be used to vary the type of tissue disruption performed, the texture of the adjacent tissue at the border of the disrupted tissue, and the quantity of disrupted tissue which tends to be lodged between the blades and removed together with the device after use.

Referring again to the blade structure of FIGS. 8A-8C, blades 48 as illustrated here have predefined flexion regions 60 which allow parts of the blades to flex. This feature is particularly valuable in cases where blades 48 span a dimension perpendicular to axis of rotation 14 greater than a given maximum internal dimension of the conduit through which they are introduced. As shown in FIGS. 9A and 9B, flexibility of the blades allows them to flex for insertion along conduit 100 and then to return to their intended dimensions on leaving the conduit, ready for use.

A range of other possible implementations of tissue disruptors 12 are illustrated in FIGS. 16A-21, and are mostly self-explanatory. The examples include various configurations of cutting wires or strips (FIGS. 16A, 16E and 17A-18B) and various other rigid cutter forms (FIGS. 16B-16D and 21) and a brush-like form (FIG. 20). In the examples of FIGS. 17A-17B, 18A-18B and 19A-19B, the cutters each have a low-profile form for insertion through the conduit and a larger-diameter open cutting form. Generally, the transition between these forms may occur either elastically, simply by being squeezed into the conduit, or may be actuated by a suitable actuator element (not shown). Particularly in the case of FIGS. 19A-19B, the cutter is formed with a base portion 62 mounted for rotation together with rotating shaft 46 and one or more pivotal portion 64 pivotally mounted relative to the base portion so as to be displaceable between a folded position (FIG. 19A) folded towards the rotating shaft and a cutting position (FIG. 19B) extended away from the rotating shaft. A biasing element (not shown) is deployed to bias the pivotal portion towards the folded position such that, during rotation of the rotating shaft, the blade opens under the effect of centripetal force to the cutting position and, when stopped, the blade is biased towards the folded position.

Although described thus far in the context of a rotary tissue disruptor which has a single rigid rotating shaft 46, it should be noted that various implementations of the present invention may use a rotary tissue disruptor which has either a segmented or flexible rotary shaft. In such cases, the aforementioned axis of rotation 14 is taken to be the axis of rotation at the proximal end of the tissue disruptor structure.

By way of example of a tissue disruptor with a segmented or flexible rotary shaft, reference is now made to FIGS. 22A-24. Specifically, FIGS. 22A and 22B illustrate a tissue disruptor 12 in which rotating shaft 46 is subdivided into three segments 46a-46c interconnected by flexible drive linkages 66. The end of distal segment 46c is pivotally anchored at a hinge 68 while being still free to rotate about its longitudinal axis. Similarly, the proximal end of proximal segment 46a is pivotally anchored by a pin-in-slot arrangement 70 while being free to rotate about its longitudinal axis. When rotary drive shaft 36 is advanced, pin-in-slot arrangement 70 allows the tissue disruptor to transform from the state of FIG. 22A to that of FIG. 22B, performing an arching motion of the segments, and sweeping through a D-shaped volume of tissue. It will be noted that the proximal segment 46a performs a motion fully analogous to that described above with reference to the earlier embodiments, and answers to the same geometric definitions used there. When rotary drive shaft 36 is retracted, the device returns to the configuration of FIG. 22A.

As in previous embodiments, segments 46a-46c are preferably provided with a plurality of radially projecting and axially spaced blades 48, such as those illustrated in FIGS. 22C and 22D.

Figure 24:
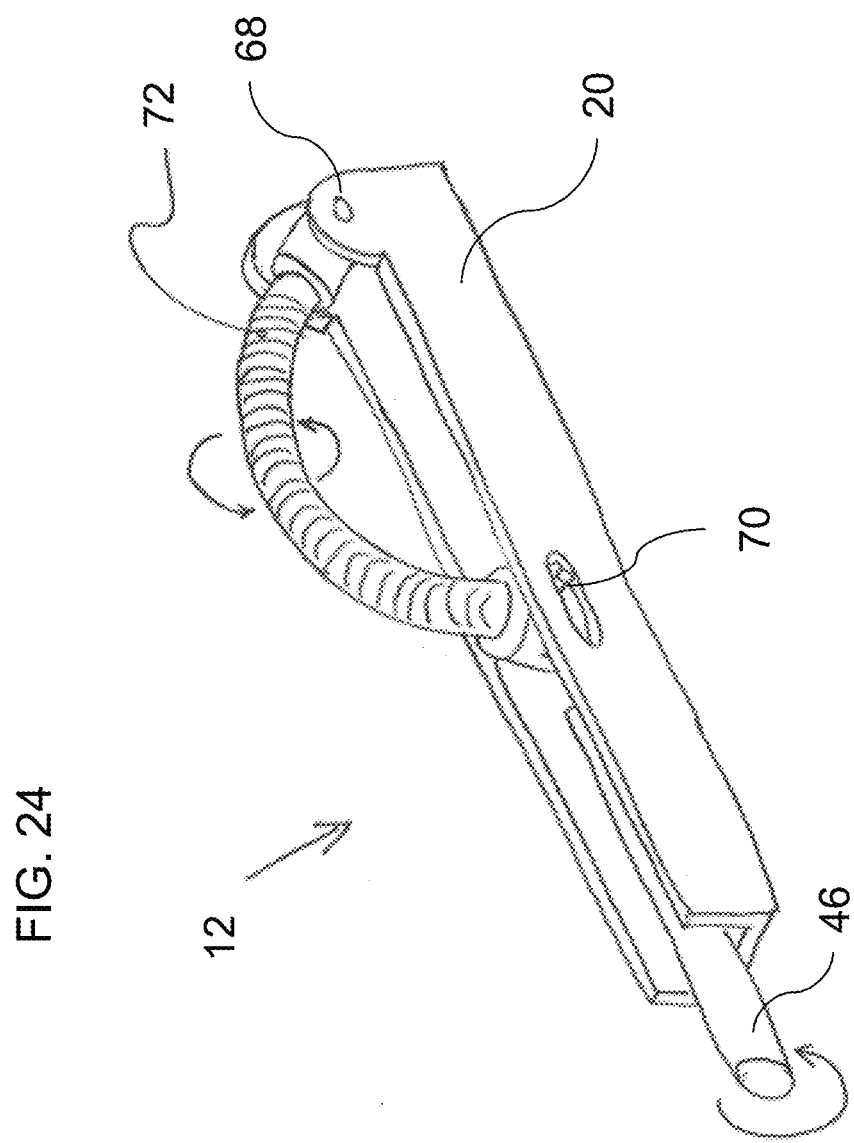
FIG. 24 is a schematic isometric view of a variant of the devices of FIGS. 22A and 23A in which tissue disruption is performed by a suitably modified flexible shaft without identifiably distinct segments.

FIGS. 23A-23C illustrate a further embodiment similar to that of FIGS. 22A-22D except that the segments here are all mounted on a common flexible shaft 72. In the version of FIG. 24, flexible shaft 72 itself becomes the direct support for the various blades (not shown) or other structures for disrupting tissue. In the latter case, the tangential direction at the proximal end of flexible shaft 72 is taken to be the "axis of rotation" of the tissue disruptor for the purpose of the geometrical definition of the present invention.

It will be appreciated that the various devices described herein are of value in a range of procedures, and corresponding methods, for disrupting target tissue in a human or animal body in various contexts and for various purposes. In use, rigid conduit 100 is first introduced into the body and fixed in a position with the distal opening adjacent to the target tissue. Tissue disruptor 12 is then introduced through the rigid conduit so that at least part of the rotary tissue disruptor projects from the distal opening. Both the rotary drive and the angular displacement mechanism are then actuated so that the rotary tissue disruptor rotates at a plurality of positions within the range of angular motion, thereby disrupting the target tissue. Most preferably, rotation of the tissue disruptor occurs continuously during the angular motion.

As mentioned, the technique of the present invention may be used to advantage on soft target tissue, and in particular, at least part of an intervertebral disc, as well as hard target tissue, and in particular, bone. It may also be advantageously used to disrupt a tumor.

Depending on the nature of the procedure being performed, at least part of the target tissue may be removed, during or after the tissue disruption process, either by application of suction via the rigid conduit or by removal of at least part of the target tissue through removal of the rotary tissue disruptor with a quantity of the target tissue lodged therein.

It will be appreciated that the above descriptions are intended only to serve as examples, and that many other embodiments are possible within the scope of the present invention as defined in the appended claims.

We claim:

1. A tissue disruption system comprising:
   a rigid conduit having an open proximal end, a distal opening and a direction of elongation, and;
   a tissue disruption device for deployment via said conduit, the tissue disruption device comprising:
   (a) a rotary tissue disruptor having a rotating shaft extending along an axis of rotation and at least one cutting element projecting laterally from said shaft, said rotary tissue disruptor being configured for insertion along the rigid conduit with said axis of rotation parallel to the direction of elongation;
   (b) an elongated member deployable so as to extend through said conduit and linked so as to support said rotary tissue disruptor during insertion of said rotary tissue disruptor along said conduit;
   (c) an angular displacement mechanism associated with said rotary tissue disruptor and configured to selectively displace said rotary tissue disruptor such that said axis of rotation sweeps through a range of angular motion; and
   (d) a rotary drive linked to said rotary tissue disruptor so as to drive said rotary tissue disruptor in rotary motion while said rotary tissue disruptor is at a range of angular positions within said range of angular motion,
   wherein said tissue disruption device mechanically interacts with said conduit such that linear displacement of said rotary tissue disruptor parallel to said direction of elongation is prevented or is limited to a predefined range of displacement during said angular motion,
   wherein at least part of said rigid conduit has a non-circular cross-section with at least one flat side, and wherein at least part of said elongated member has a non-circular cross-section with a corresponding at least one flat side, such that engagement of said cross-section of said elongated member within said cross-section of said rigid conduit limits angular motion of said tissue disruption device about said direction of elongation.

2. The tissue disruption system of claim 1, wherein said angular displacement mechanism generates angular motion of said rotary tissue disruptor within a plane including the direction of elongation of the conduit.

3. The tissue disruption system of claim 1, wherein said angular displacement mechanism generates angular motion that is asymmetric relative to the direction of elongation of the conduit.

4. The tissue disruption system of claim 1, wherein said angular displacement mechanism generates angular motion of said rotary tissue disruptor through an angle of at least 30 degrees.

5. The tissue disruption system of claim 1, wherein said angular displacement mechanism generates angular motion of said rotary tissue disruptor through an angle of at least 45 degrees.

6. The tissue disruption system of claim 1, wherein said angular displacement mechanism includes a pivotal linkage at least partially defining a path of said angular motion.

7. The tissue disruption system of claim 1, wherein said angular displacement mechanism includes an elongated actuator deployable so as to extend along said conduit and linked to said rotary tissue disruptor such that relative displacement of said elongated actuator and said elongated member actuates said angular motion of said rotary tissue disruptor.

8. The tissue disruption system of claim 7, wherein said elongated actuator is a rotary drive shaft linking said rotary drive to said rotary tissue disruptor.

9. The tissue disruption system of claim 1, further comprising a rotary drive shaft deployable so as to extend through said conduit and linking said rotary drive to said rotary tissue disruptor.

10. The tissue disruption system of claim 1, wherein said rotary drive comprises at least one miniature motor deployed in proximity to said rotary tissue disruptor for insertion along the conduit.

11. The tissue disruption system of claim 1, wherein said rotary drive comprises at least one miniature motor integrated with said rotary tissue disruptor so as to undergo angular motion together with said rotary tissue disruptor.

12. The tissue disruption system of claim 1, wherein said tissue disruption device mechanically interacts with said conduit such that linear displacement of said rotary tissue disruptor parallel to said direction of elongation is prevented during said angular motion.

13. The tissue disruption system of claim 1, wherein said distal opening includes an open tip of said conduit.

14. The tissue disruption system of claim 1, wherein a distal tip of said conduit is closed, and wherein said distal opening is implemented as a lateral opening proximal to said distal tip.

15. The tissue disruption system of claim 1, wherein said at least one cutting element comprises a plurality of blades projecting radially from, and spaced along, said shaft.

16. The tissue disruption system of claim 15, wherein said plurality of blades include at least a first blade having a first radial length and at least a second blade having a second radial length smaller than said first radial length.

17. The tissue disruption system of claim 15, wherein said plurality of blades include blades of differing radial lengths arranged such that an intermediate region along a length of said rotating shaft has blades of a first radial length and regions distal and proximal to said intermediate region have blades of a second radial length smaller than said first radial length.

18. The tissue disruption system of claim 15, wherein said conduit has a given maximum internal dimension, and wherein said plurality of blades span a dimension perpendicular to said axis of rotation greater than said given maximum internal dimension, at least a subset of said blades being formed with a predefined flexion region configured to allow flexing of a part of said blades for insertion along said conduit.

19. The tissue disruption system of claim 15, wherein said rotating shaft terminates in a rounded non-cutting tip.

20. The tissue disruption system of claim 15, wherein at least one of said plurality of blades comprises:
   (a) a base portion mounted for rotation together with said rotating shaft;
   (b) a pivotal portion pivotally mounted relative to said base portion so as to be displaceable between a folded position folded towards said rotating shaft and a cutting position extended away from said rotating shaft; and (c) a biasing element deployed to bias said pivotal portion towards said folded position such that, during rotation of said rotating shaft, said blade opens under the effect of centripetal force to said cutting position and, when stopped, said blade is biased towards said folded position.

21. A method employing the tissue disruption system of claim 1 for disrupting target tissue in a human or animal body, the method comprising the steps of:
   (a) introducing said rigid conduit into the body, the conduit having an open proximal end and a distal opening, the conduit being fixed in a position with said distal opening adjacent to said target tissue;
   (b) introducing through said rigid conduit said tissue disruption device so that at least part of said rotary tissue disruptor projects from said distal opening; and
   (c) actuating both said rotary drive and said angular displacement mechanism so that said rotary tissue disruptor rotates at a plurality of positions within said range of angular motion, thereby disrupting said target tissue.

22. The method of claim 21, wherein said target tissue includes at least part of an intervertebral disc.

23. The method of claim 21, wherein said target tissue is soft tissue.

24. The method of claim 21, wherein said target tissue is bone.

25. The method of claim 21, wherein said target tissue is hard tissue.

26. The method of claim 21, wherein said target tissue is a tumor.

27. The method of claim 21, further comprising removing at least part of the target tissue by application of suction via said rigid conduit.

28. The method of claim 21, further comprising removing at least part of the target tissue through removal of said rotary tissue disruptor with a quantity of the target tissue lodged therein.

29. A method for disrupting target tissue in a human or animal body, the method comprising the steps of:
   (a) providing a tissue disruption device comprising:
      (i) a rotary tissue disruptor having a rotating shaft extending along an axis of rotation and at least one cutting element projecting laterally from said shaft, said rotary tissue disruptor being configured for insertion along a rigid conduit with said axis of rotation parallel to a direction of elongation of the conduit;
      (ii) an elongated member deployable so as to extend through the conduit and linked so as to support said rotary tissue disruptor during insertion of said rotary tissue disruptor along the conduit;
      (iii) an angular displacement mechanism associated with said rotary tissue disruptor and configured to selectively displace said rotary tissue disruptor such that said axis of rotation sweeps through a range of angular motion; and
      (iv) a rotary drive linked to said rotary tissue disruptor so as to drive said rotary tissue disruptor in rotary motion while said rotary tissue disruptor is at a range of angular positions within said range of angular motion,
   (b) introducing a rigid conduit into the body, the conduit having an open proximal end and a distal opening, the conduit being fixed in a position with said distal opening adjacent to said target tissue;
   (b) introducing through said rigid conduit said tissue disruption device so that at least part of said rotary tissue disruptor projects from said distal opening; and
   (c) actuating both said rotary drive and said angular displacement mechanism so that said rotary tissue disruptor rotates at a plurality of positions within said range of angular motion, thereby disrupting said target tissue,
wherein said tissue disruption device mechanically interacts with said conduit such that linear displacement of said rotary tissue disruptor parallel to said direction of elongation is prevented or is limited to a predefined range of displacement during said angular motion,
wherein at least part of said rigid conduit has a non-circular cross-section with at least one flat side, and wherein at least part of said elongated member has a non-circular cross-section with a corresponding at least one flat side, such that engagement of said cross-section of said elongated member within said cross-section of said rigid conduit limits angular motion of said tissue disruption device about said direction of elongation.

30. The tissue disruption system of claim 1, wherein at least part of said rigid conduit has a rectangular cross-section, and wherein at least part of said elongated member has a rectangular cross-section, such that engagement of said rectangular cross-section of said elongated member within said rectangular cross-section of said rigid conduit limits angular motion of said tissue disruption device about said direction of elongation.

31. A tissue disruption system comprising:
   a rigid conduit having an open proximal end, a distal opening and a direction of elongation, and;
   a tissue disruption device for deployment via said conduit, the tissue disruption device comprising:
      (a) a rotary tissue disruptor having a rotating shaft extending along an axis of rotation and at least one cutting element projecting laterally from said shaft, said rotary tissue disruptor being configured for insertion along the rigid conduit with said axis of rotation parallel to the direction of elongation;
      (b) an elongated member deployable so as to extend through said conduit and linked so as to support said rotary tissue disruptor during insertion of said rotary tissue disruptor along said conduit;
      (c) an angular displacement mechanism associated with said rotary tissue disruptor and configured to selectively displace said rotary tissue disruptor such that said axis of rotation sweeps through a range of angular motion; and
      (d) a rotary drive linked to said rotary tissue disruptor so as to drive said rotary tissue disruptor in rotary motion while said rotary tissue disruptor is at a range of angular positions within said range of angular motion,
wherein said tissue disruption device mechanically interacts with said conduit such that linear displacement of said rotary tissue disruptor parallel to said direction of elongation is prevented or is limited to a predefined range of displacement during said angular motion, and such that said tissue disruption device is prevented from rotating relative to said conduit about said direction of elongation,
and wherein at least part of said rigid conduit has a rectangular cross-section, and wherein at least part of said elongated member has a rectangular cross-section, such that engagement of said rectangular cross-section of said elongated member within said rectangular cross-section of said rigid conduit limits angular motion of said tissue disruption device about said direction of elongation.

* * * * *